United States Patent [19]

Etess

[11] 4,190,368
[45] Feb. 26, 1980

[54] SULFUR MONITOR ANALYZER

[75] Inventor: Edward Etess, San Diego, Calif.

[73] Assignee: Monitor Labs, Inc., San Diego, Calif.

[21] Appl. No.: 916,911

[22] Filed: Jun. 19, 1978

[51] Int. Cl.² .......................... G01J 3/50; G01N 21/58
[52] U.S. Cl. .................. 356/417; 250/361 C; 422/52
[58] Field of Search .............................. 356/315, 417; 250/361 C; 422/52

[56] References Cited

U.S. PATENT DOCUMENTS

| | | | |
|---|---|---|---|
| 3,486,827 | 12/1969 | Binek et al. | 356/417 |
| 3,489,498 | 1/1970 | Brody et al. | 356/417 |
| 3,967,933 | 7/1976 | Etess et al. | 250/361 C X |

OTHER PUBLICATIONS

Monitor Labs Instruction Manual for Sulfur Monitor Model 8450, published Jan. 12, 1977.

Primary Examiner—F. L. Evans
Attorney, Agent, or Firm—Oblon, Fisher, Spivak, McClelland & Maier

[57] ABSTRACT

A sulfur monitor analyzer is disclosed and utilizes a burner or flame holder, a burner or reaction chamber, a photomultiplier tube, a light collimator, and chopper blade members with openings so as to permit a flame disposed in the burner or reaction chamber to be seen by the photomultiplier tube at all times. A chemiluminescent radiation mask is disposed operatively between a portion of the chemiluminescent radiation and the photomultiplier tube so as to provide a chopper open mode of operation at which time the photomultiplier tube receives the flame radiation and a fraction of any chemiluminescent radiation surrounding the flames with any remaining fraction of any chemiluminescent radiation being obscured permanently by the chemiluminescent radiation mask. When the chopper is in the closed mode of operation, the photomultiplier tube receives only the radiation from the flame through an aperture defined by an opening in the opaque segment of this chopper or chemiluminescent radiation mask.

11 Claims, 9 Drawing Figures

SULFUR MONITOR ANALYZER

BACKGROUND OF THE INVENTION

1. Field of the Invention

The present invention relates to gas analyzers, and more particularly to an analyzer for gases containing sulfur compounds, by utilizing a chemical reaction which produces light by chemiluminescence.

2. Description of the Prior Art

Gas analysis performed utilizing flame photometry is known by burning a sample of the gas to be analyzed in an air flame surrounded by hydrogen, restricting light emissions arising from materials in the sample to substantially only those which radiate energy from a region above the flame, and detecting selectively wave lengths of radiant energy emanating from the region above the flame at selected emission wave lengths characteristic of sulfur or phosphorous chemiluminescence, or both.

SUMMARY OF THE INVENTION

An object of the present invention is to provide an analyzer for performing a continuous dry analysis of compounds.

A further object of the present invention is to provide a flame photometric detection device which performs a continuous dry analysis of sulfur compounds based on the chemiluminescence of an activated molecular sulfur species produced by a hydrogen hyperventilated air diffusion flame.

According to the present invention, the foregoing and other objects are attained by providing a flame holder, a flame chamber within which the flame holder is disposed, a mechanism for obtaining continuously and transferring the sample to the flame holder, a mechanism for transferring continuously hydrogen to the flame chamber thus causing a flame and associated chemiluminescence, a mechanism for measuring the intensity of the chemiluminescence emission which is proportional to the sulfur compound concentration in the sample, and an optical shutter mechanism disposed between the flame chamber and the light intensity measuring mechanism for exposing alternately the flame and the chemiluminescent emissions and obscuring the chemiluminescence from the flame chamber to the light intensity measuring device. Also in accordance with the present invention, the concentration of sulfur compounds in air is measured by continuously introducing the air sample into a flame chamber, continuously reacting the sample for causing characteristic chemiluminescence, periodically exposing and obscuring chemiluminescent emission or radiation while continuously exposing the flame, and continuously measuring light emission intensity resulting from the periodically exposed and obscured chemiluminescent emission and the continuously exposed flame.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views, and wherein.

DETAILED DESCRIPTION OF THE PREFERRED EMBODIMENT

The sulfur analyzer is a flame photometric detection (FPD) device which performs continuous dry analysis of sulfur compounds. Its operation is based on the chemiluminescence of an activated molecular sulfur species produced by a hydrogen hyperventilated diffusion flame. A photomultiplier tube (PMT) measures the chemiluminescent emission intensity level.

Figure 1:
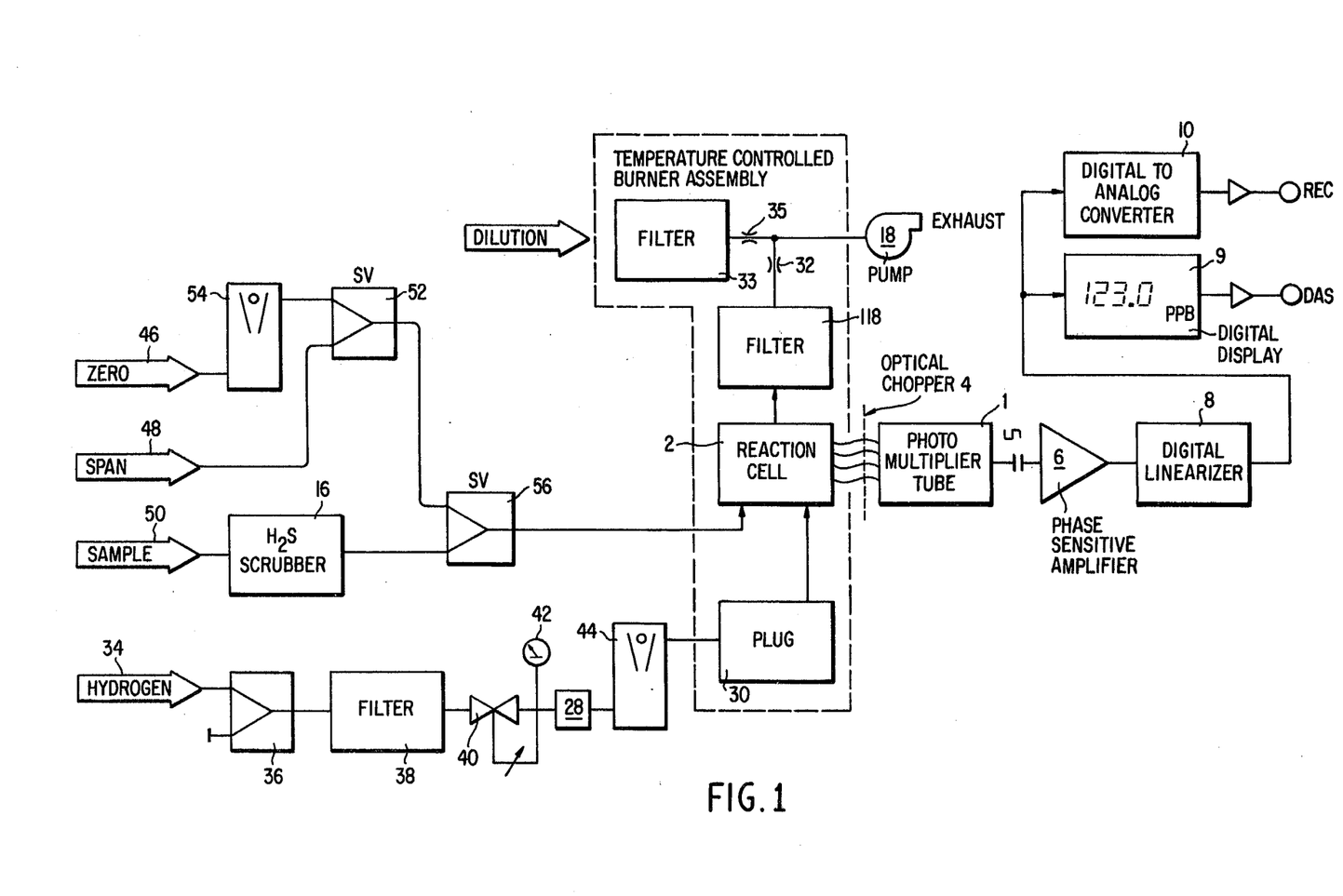
FIG. 1 is a schematic representation of the sulfur analyzer of the present invention.

FIG. 1 is the over-all sulfur monitor schematic. Hydrogen and air enter and leave the burner through the pneumatic network. The chemiluminescent emission in the burner or reaction chamber 2, is interrupted and transmitted alternately to photomultiplier tube (PMT) by an optical chopper 4 at a rate of 36 times per second. A phase-sensitive amplifier 6 processes the PMT signal which is subsequently linearized by digital techniques. A digital-to-analog converter 10 operates on the digitized signal in preparation for analog and DAS outputs.

Figure 6:
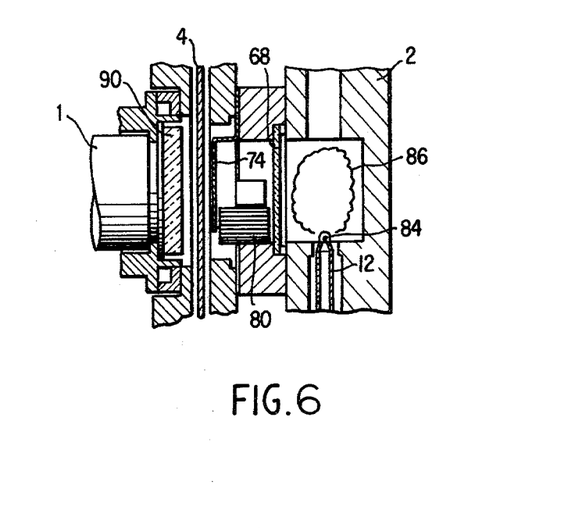
FIG. 6 is a cross-sectional view of the combined photomultiplier tube, chopper assembly and burner chamber assembly.

The FPD comprises three basic functional subsystems: (1) the sample nozzle or flame holder 12 (as shown in FIG. 6), (2) burner, flame, or reaction chamber 2, and (3) the photomultiplier tube 1. Air containing the sulfur molecules enters through the sample nozzle which also holds the flame. The flame 84 is surrounded by hydrogen which is enclosed by flame chamber 2. One wall of the flame chamber 2 is a clear optical window through which photomultiplier tube 1 measures the chemiluminescent emission energy intensity level and converts it to an equivalent electrical signal.

Figure 2:
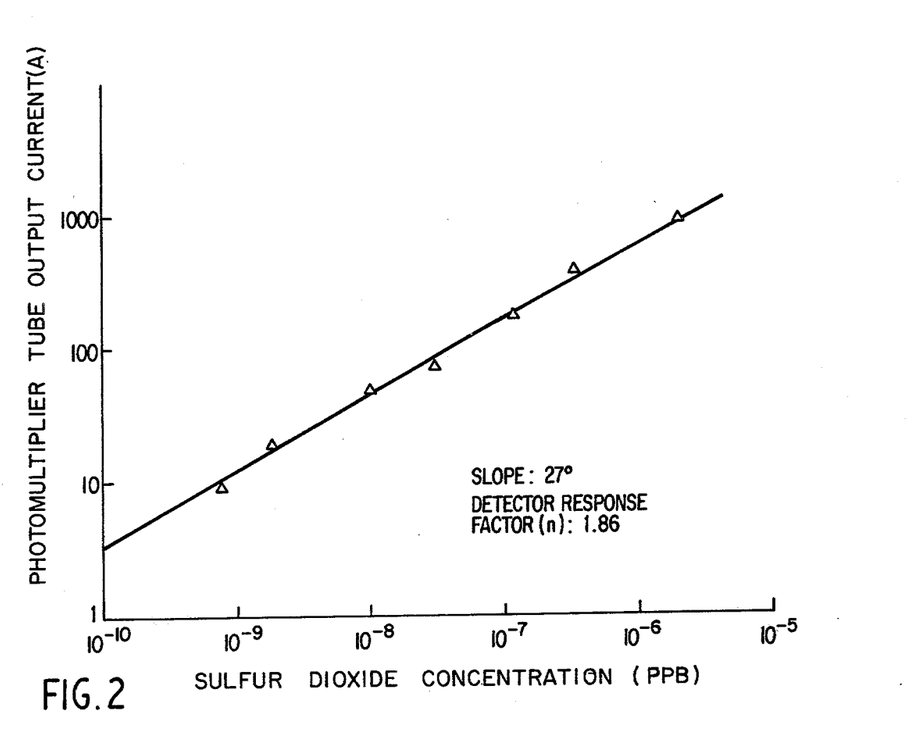
FIG. 2 is a chart indicating the flame photometric detector sulfur response characteristics.

Emission intensity is directly proportional to the photomultiplier tube current. Examination of FIG. 2 shows that the slope of the relationship is 1.86.

Figure 3:
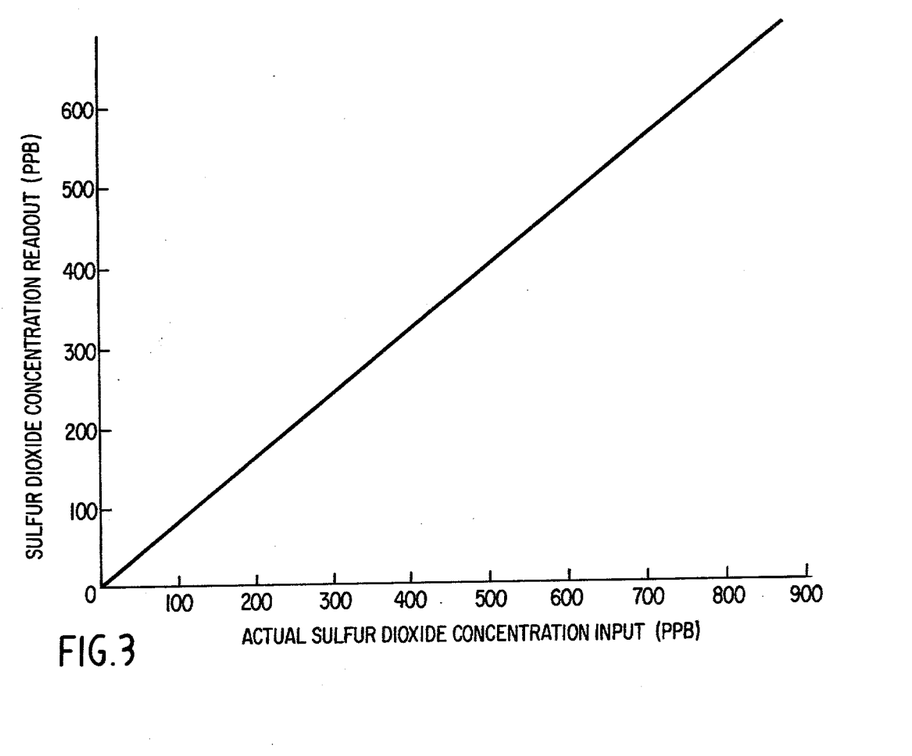
FIG. 3 is a chart setting forth the flame photometric detector sulfur monitor linearity.

To obtain a more convenient output form, the sulfur analyzer contains a digital linearizer 8 which processes electronically the photomultiplier tube signal to yield a linear output as shown by FIG. 3 and on associated digital display 9.

The exhaust gases flow out of the burner chamber into the exhaust manifold, which is maintained at 457.2–508 mm Hg (18–20″ Hg) vacuum. At this stage they are mixed with approximately 8–10 l/min. of dilution air which enters through the dilution air critical orifice 35 in the exhaust manifold. The diluted exhaust gas is transported from the manifold, to the vacuum pump 18, and out of the analyzer through the exhaust port fitting.

During operation the exhaust gas is composed nominally of 43, 144 and 72 ml/min. of hydrogen, nitrogen and water vapor, respectively. Downstream of the exhaust orifice it is mixed with 9000 ml/min. of dilution air to yield a hydrogen concentration of 0.46 percent by volume. In the event the flame does not ignite, the exhaust gas is composed of 120 and 180 ml/min. of hydrogen and air, respectively. After mixing with the exhaust dilution air the hydrogen concentration is reduced to 1.3 percent. In both cases the hydrogen concentration entering the vacuum pump and discharged from the analyzer exhaust is below the lower hydrogen explosion concentration limit (4.1 percent) in air.

The burner is ignited remotely or manually by a pushbutton without adjusting gas flowrates. The system will automatically enter a reignite sequence upon a flameout for any reason including a power failure. However, a thermal interlock between the burner assembly and the ignition activation circuit is included to prevent ignition until the burner assembly is above 95° C. A heater supplies the energy to preheat the burner assembly with power to the analyzer. The ignition sequence is not activated until the burner assembly is above 95° C. It is essential that the burner assembly temperature be always in excess of 80° C. to prevent water vapor condensation within the burner chamber, exhaust orifice, and/or exhaust assembly. Otherwise, liquid water deposits will plug and obstruct gas flow at the exhaust orifice, fog the flame chamber window and change the analyzer calibration, and/or promote corrosion and subsequent plugging.

For most FPD analyzers, the user must wait a given length of time prior to igniting the burner. More important, however, units equipped with an auto-restart feature must also include a time-delay in their ignition sequence when restarting after a power failure. With a power-down time of sufficient length to permit the burner assembly to cool below 95° C., sufficient time must be allowed to preheat the burner assembly after power resumes to avoid water vapor condensation. The burner-ignition circuit thermal interlock feature eliminates the water vapor condensation possibility under all circumstances.

Chopper-stabilized electronics of the present invention are mandatory for low zero stability and accurate low level measurements. One advantage of this is elimination of photomultiplier dark current as a source of zero drift. Although PMT dark current may be nulled electronically for any given value, it has an exponential temperature coefficient which requires a highly stable PMT temperature control for a direct coupled system. In a chopper stabilized system, the PMT cooler can be operated at maximum capacity thereby minimizing PMT noise without affecting zero drift.

In addition, high gain amplification of the signal prior to demodulation eliminates zero drift due to electronic component temperature coefficients and aging.

Recent developments in low cost digital circuitry make it possible to eliminate many of the severe shortcomings associated with analog linearization techniques.

A subtle but significant drawback of the log/antilog amplifier system is its anomalous behavior near zero. Since the gain is very high and the log amplifier will not process zero or negative signals, random noise will be rectified producing an offset equivalent to about 5 ppb. Digital linearization permits the processing of zero signals, thus reducing the apparent zero noise offset and providing more accurate stable measurements of low sulfur concentrations.

Hydrogen flow rate control is performed by maintaining a constant upstream pressure across a two step pneumatic impedance element. The hydrogen pressure regulator 26 and the porous stainless steel plugs 28,30 shown by FIG. 1 are introduced to the hydrogen stream for these purposes.

Since the gas density and viscosity are the main parameters affecting pneumatic impendance, temperature controlling the second porous plug 30 maintains the degree of constant impedance required. The control is accomplished by locating the second plug 30 in the sample nozzle or flame holder 12 which itself is temperature controlled.

A constant burner exhaust gas flowrate is maintained by the pneumatic impedance element in the exhaust stream which consists of a temperature-controlled critical orifice 32 contained within the exhaust manifold which is thermally coupled to the flame channel 2. This is achieved with the temperature-controlled critical orifice assembly ensuring that the pressure downstream of the orifice 32 is always maintained at an absolute pressure less than $\frac{1}{2}$ of the orifice upstream pressure. For standard conditions, a vacuum of 0.5625 kg/cm$^2$ (8 psig) is sufficient to maintain the critical flow condition.

Hydrogen gas is introduced at the analyzer "H$_2$" port 34. It is transported to a normally closed solenoid shut-off valve 36, the pressure regulator 26, including a filter 38, valve 40 and pressure gauge 42, the first porous plug 28, hydrogen rotameter 44, to the second porous plug 30 and the burner chamber 2.

Figure 4:
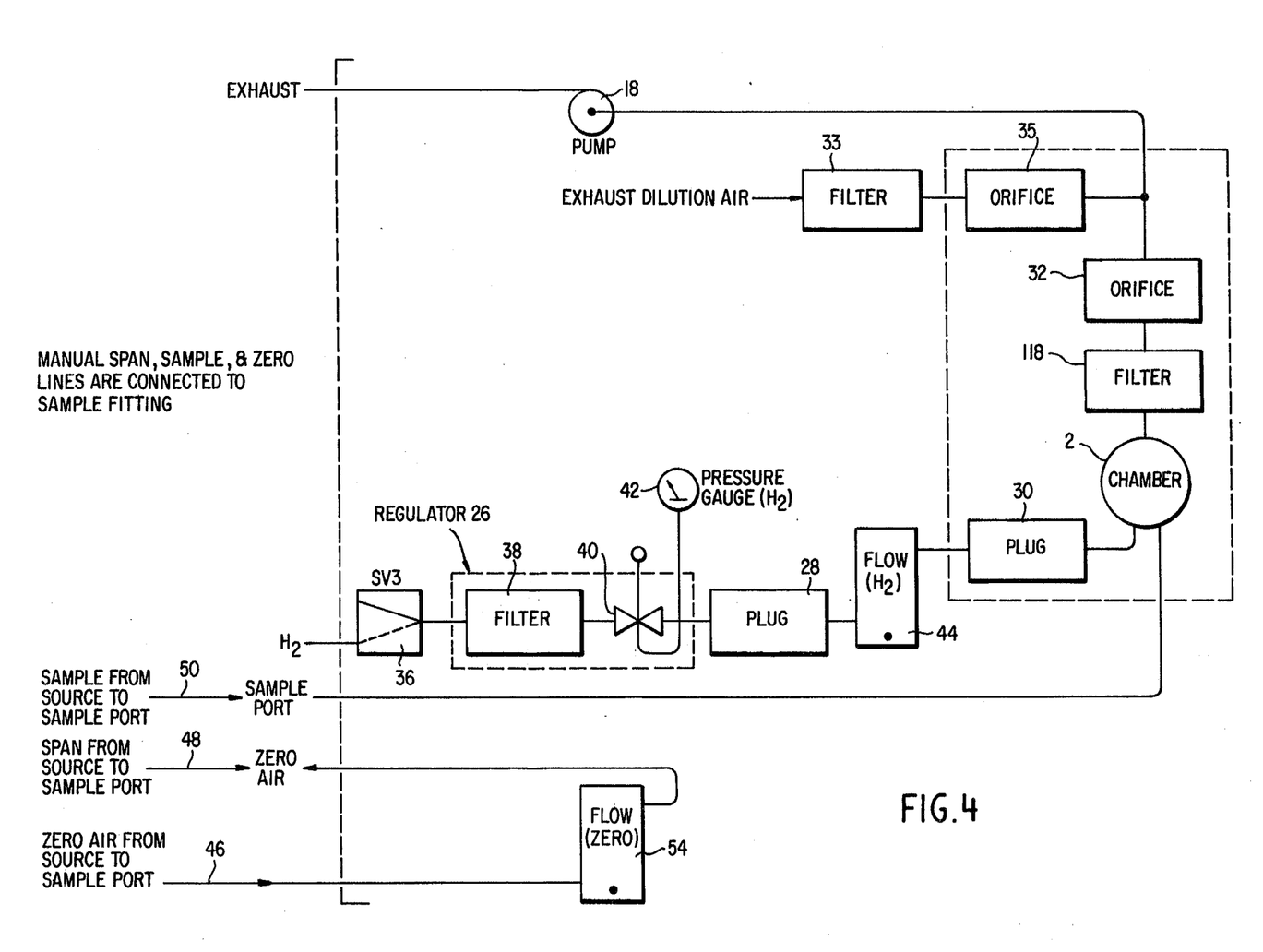
FIG. 4a is an exploded view of the burner assembly of the embodiment set forth in FIG. 1.
FIG. 4b shows the detail of gas flow through the sample nozzle of the present invention.

As shown by FIG. 1, the sample stream enters through the sample port. A line leading directly from and through the "SAMPLE" port transports the sample. For this configuration, it is noted that zero, span, and sample gas all enter through a common "SAMPLE" port. Sample is measured in this configuration by introducing zero gas through the zero port to the analyzer air flow meter and out through the span port to the external zero valve as shown. Thus the user will be able to obtain a measurement of sample air flowrate to the burner. Span gas is introduced at the external valve as shown by FIG. 4. As stated earlier, all gases enter the burner through the "SAMPLE" port.

The burner zero output level is gas pressure sensitive, i.e., the output signal of zero air will respond to inlet gas pressure. Therefore, it is important that the pneumatic impedance of each gas line 46,48 and 50 respectively, from the sample, span and zero gas sources to the burner are matched within 24.5 mm (1") H$_2$O.

As shown in FIG. 1, zero line 46 and span line 48 interconnect with solenoid three-way valve 52 with a rotameter 54 being interconnected between zero line 46 and valve 52. Valve 52 in turn connects with a similar three-way valve 56, the sample line 50, which is interconnected with hydrogen scrubber 16, and three-way solenoid valve 56.

Figure 4A:
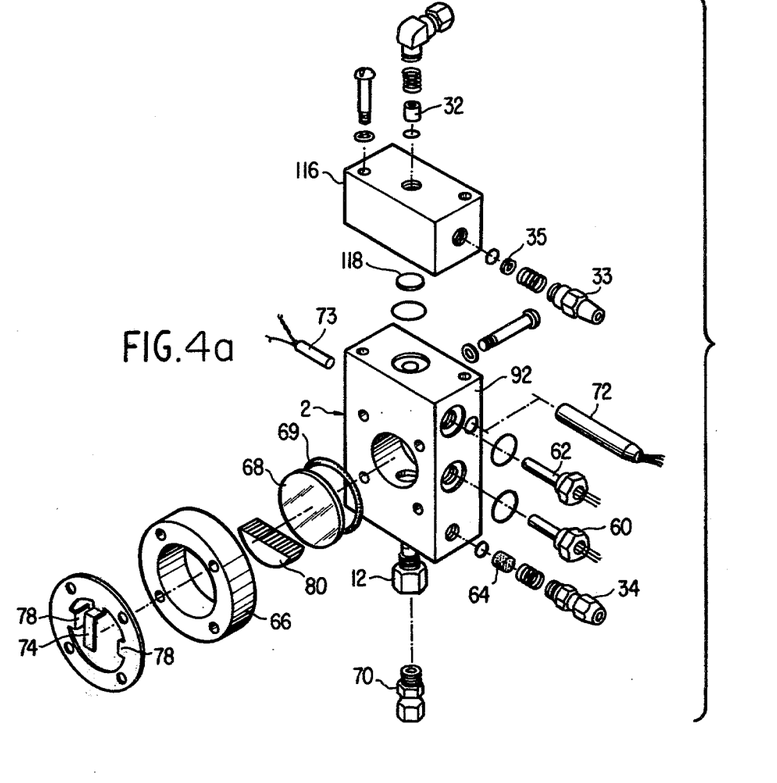
Figure 4B:
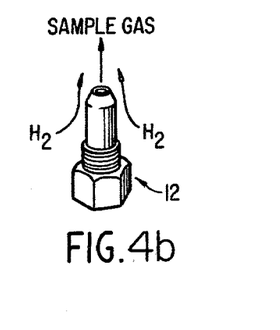
Figure 5:
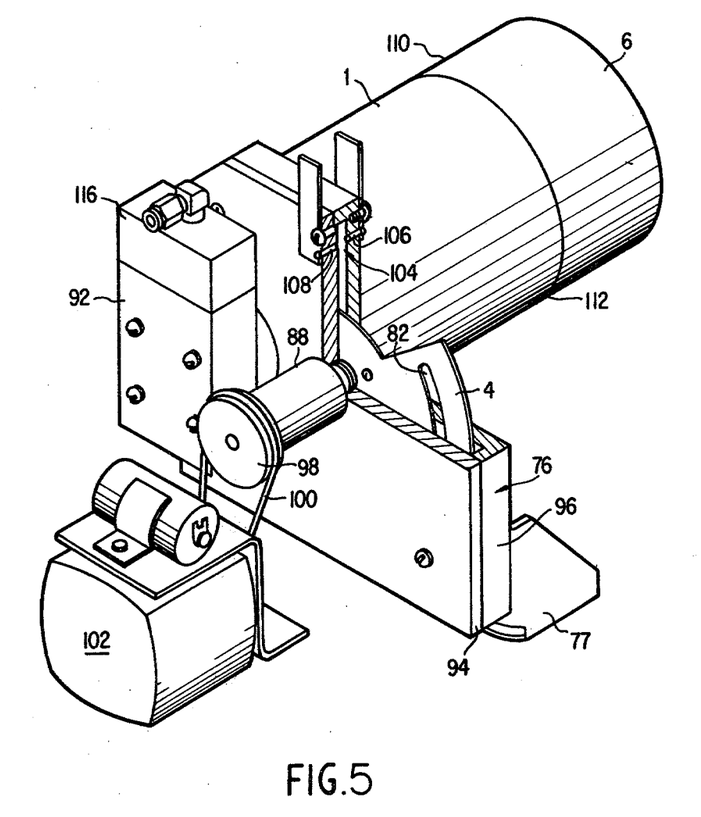
FIG. 5 sets forth a perspective view of the chopper assembly of the embodiment set forth in FIG. 1.

The burner assembly comprises the sample nozzle 12, burner chamber 2, ignitor 60, flame-off detector 62, hydrogen flow restrictor 64 and the exhaust assembly with exhaust and dilution air flow rate control elements. FIG. 4a shows the burner assembly and its components, while FIG. 4b shows the flow of sample gas and H$_2$ with respect to sample nozzle 12. The burner is attached to the chopper by four stainless steel screws through a thermal insulating adaptor ring 66 as illustrated by FIG. 5.

Dilution air is induced in the exhaust manifold through an integral filter 33 without an external connection. Hydrogen enters through an inlet which includes a tube swaged brass fitting 34 near the bottom of one side of the burner chamber. A porous stainless steel plug flow restrictor 64 is inserted in the burner hydrogen fitting cavity.

The sample air connection is a tube swaged stainless steel fitting 70 attached to a black TFE line.

The burner chamber 2 is cylindrical and disposed within housing 92 with one end bounded by a borosilicate window 68 sealed by O-ring 69. All other surfaces are white TFE coated for easy cleaning and to ensure surface inertness.

A chemiluminescent radiation mask 74 is introduced between the chopper 4 and the burner chamber 2. It is fabricated from non-reflective aluminum sheet and secured to the chopper housing 76 by means of the burner mounting screws. Its main feature is a circular frame member with inner and outer circumferential edge portions provided with diametrically projecting chemiluminescent radiation mask (or tab) 74 located along the arc exposed by the opening 82 in the chopper blade 4 and which extends from the inner circumferential edge portion of the circular frame. This tab is mounted close to the chopper plane and extends downward along substantially the entire diameter of the circular frame from the top of the burner window 68 to a point adjacent the top of the flame. A secondary feature of this part is the two "ears" 78 which serve to secure the flame collimator 80.

Figure 7A:
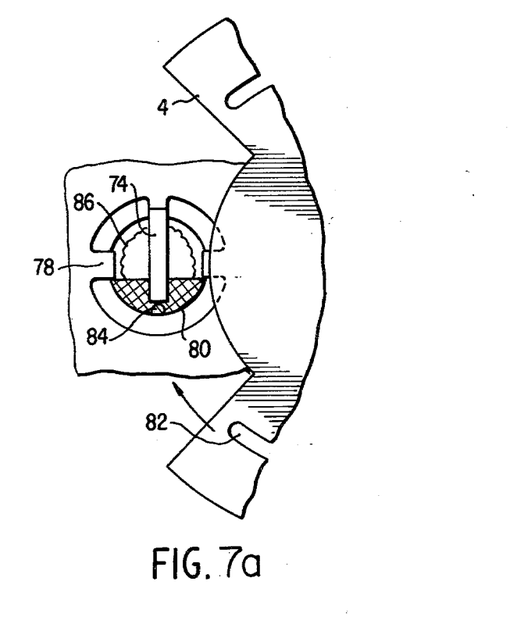
FIGS. 7a and 7b illustrate the chopper open and chopper closed mode of operation of the present invention, respectively.

The flame collimator 80 is introduced between the chemiluminescent mask 74 and the burner window 68 and is shown in FIG. 7a. It is fabricated from bright aluminum honeycomb. It extends along the optical axis of the system and its segmental shape fits the lower third of the burner window 68. It is held in place by the "ears" 78 located on the mask 74. An optical filter 90 may also be provided adjacent to PMT 1 as shown in FIG. 6.

Sample gas enters through the sample nozzle 12 at the bottom of the chamber. Hydrogen enters through the annular space concentric with the sample nozzle. The hot wire ignitor 60 and the thermocouple flame-off detector 62 are recessed in cavities in the top half side of the burner chamber 2. A temperature sensor 73 and burner block heater 72 are embedded in the burner housing 92.

Combustion gases leave the chamber through the filter 118, orifice 32, and exhaust manifold 116 at the top, flowing past the flame detector thermocouple 62, and dilute air orifice 35 and associated filter 33.

Except for the sample nozzle, ignitor and flame detector all surfaces in contact with the reaction are TFE surfaces or borosilicate glass.

The sample nozzle 12 is stainless steel and embodies a carefully machined conical tip which provides the flame holder, a sealing surface, and a female pipe thread for connection to the sample inlet tube fitting 70.

The nozzle serves to separate the sample (oxidant) and annular hydrogen (fuel) streams until they enter the burner chamber 2. At the lower perimeter of the chamber 2 the gases meet and, after ignition, burn as a hydrogen hyperventilated air diffusion air flame attached to the rim of the nozzle tip.

Since chemiluminescence occurs above the flame it is essential that the flame size and its emissions levels are constant such that the flame luminescence, which is seen by the PMT as a baseline light level, is unvarying.

Burner thermal control at an elevated temperature level near 110° C. is essential to prevent exhaust gas water vapor condensation and to maintain control over hydrogen gas viscosity and the acoustic velocity at the exhaust gas and dilution air orifices.

Thermal control is obtained with an embedded heater 72 and thermistor and the temperature is maintained at 110°–115° C. by a proporational controller. A thermocouple is located adjacent to the control thermistor.

The chopper assembly is a rotating optical shutter provided with openings therein and which interrupts 36 times per second the chemiluminescent emissions irradiating the photomultiplier tube and produces an AC light signal. It contains the chopper blade and its bearings and the optical synchronizing detector. In addition, it provides the structure to which the burner and the PMT assemblies are mounted. FIG. 5 shows the chopper assembly.

The chopper 4 includes a wide, circular opening 82 located at a predetermined radius and extending almost the full circular width of each blade.

Figure 7B:
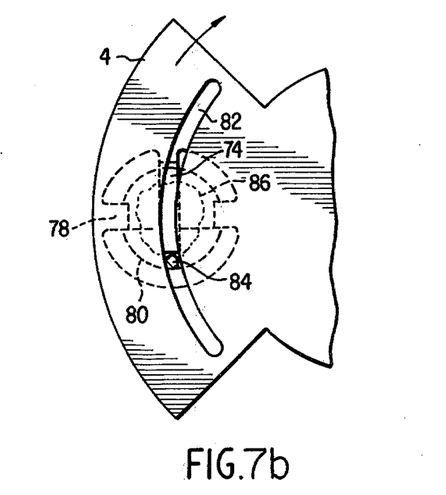

FIGS. 7a and 7b show the two alternate views of the present burner as seen by the PMT 1 with the chopper open and closed, respectively.

The arrangement permits the flame to be seen by the PMT 1 at all times. As FIGS. 7a and 7b illustrate, when the chopper is open, the PMT sees the flame 84 and a large percentage of the chemiluminescent radiation 86, the remaining percentage being permanently obscured by the mask 74. When the chopper is closed, the PMT sees the flame only (through the aperture defined by the chopper opening 82 and the mask 74). Because of the constant flame reference due to this unique chopper design, the variations in flame intensity due to water vapor variations, i.e. atmospheric pressure, etc., are greatly reduced. The purpose of the collimator 80 is to increase the efficiency of light transfer with respect to the slot 82 and mask 74.

The system is effective because a mixer assembly decodes the PMT signal as a difference between relative "light" and "dark"; or between chopper open and chopper closed modes. This occurs at a high frequency, approximately 36 cycles per second, and so variations in flame intensity which occur at a much lower frequency appear as D.C. variations and are not transmitted through the capacitive connection to the mixer card assembly.

The housing 76 is composed of a front and rear plate 94,96 respectively, which when assembled provides the chopper cavity for the chopper blade. It is light-sealed by labyrinths and by use of non-reflecting black surfaces. The housing is not pneumatically sealed and no sealing O-rings are required.

The chopper blade is a two bladed, quadrantal disc rotating at a constant speed within the cavity. It is mounted on a shaft which is supported by two shielded grease-filled ball-bearings. An external drive pulley 98 is mounted on the shaft. The bearings are within a housing 88 which is mounted to the front plate 94.

Tapped holes are provided on the front plate for mounting the burner assembly while the rear plate contains tapped holes for mounting the PMT assembly and attaching feet members 77.

The synchronous detector assembly 104 comprises two subassemblies; an LED 106 and a photo transistor 108, each mounted on small PC cards with integral connectors (not shown).

The LED assembly is mounted externally near the top of the chopper housing rear plate 96 emitting through a small collimating port in the rear plate across the path of the chopper blade.

The photo transistor detector assembly is mounted similarly opposite the LED assembly on the front plate 94 in line optically with the LED through a small port in the front plate.

The drive motor assembly is comprised of the motor 102 and drive pully 98. It is mounted to the chassis by a bracket and located at the front of the chopper housing.

The motor drives the chopper blade through a thin O-ring belt 100 at a speed determined to provide the maximum isolation from interfering frequencies. The O-ring belt is of ethylene propylene rubber, selected specially for long life in this application.

The chemiluminescent emission energy is transduced into a proportional electrical current level by the PMT 1. The preamplifier 6 performs the preliminary signal conditioning with FIG. 6 showing the assembly. The photomultiplier 1 is a 30 mm end-on tube with a peak spectral sensitivity at approximately 4000 Å.

The housing 110 mechanically supports the PMT, optically seals it and thermally isolates it from the external thermal environment. The housing 110 is a heavy-walled aluminum tube with a 3940 Å$^+$-60 Å optical band pass filter cemented in at one end. A thick polyurethane foam insulating sleeve 112 envelopes the housing 110. A platform which is coupled thermally to the PMT housing projects through a reactangular hole in the sleeve.

The pre-amp 6 is conventional and performs four important functions:

(1) Filters the high frequency components of PMT noise.

(2) Matches the impedance of the PMT output to the mixer input and coaxial cable.

(3) Cancels H.V. power supply noise.

(4) Substracts the bucking signal from the PMT signal.

Obviously, many modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A system for detecting sulfur concentrations in a gas mixture sample which comprises:
   a flame holder;
   a flame chamber within which said flame holder is disposed;
   means for continuously obtaining and transferring a portion of the sample to said flame holder;
   means for continuously transferring hydrogen to said flame chamber, thus generating a flame and causing chemiluminescent radiation;
   means for detecting light from said chemiluminescent radiation for measuring signals indicative of concentrations in the sample; and
   optical shutter means disposed between flame chamber and said light detecting means for alternately exposing and obscuring the chemiluminescent radiation emitted from said flame chamber while continually exposing the flame to said light detecting means.

2. The system as set forth in claim 1, which further comprises:
   a stationary chemiluminescent radiation mask member, secured to said flame chamber, disposed above and adjacent to said flame as well as between said reaction chamber and said means for detecting light.

3. A system as set forth in claim 1, wherein:
   said optical shutter means comprises a plurality of rotatable shutter blade members, said shutter blade members including an arcuate opening for exposing said flame and said chemiluminescent radiation such that the combination of said stationary mask member and said opening obscures said chemiluminescent radiation when said shutter blade members are disposed between said flame chamber and said means for detecting light.

4. A system as set forth in claim 1, which further comprises:
   means for collimating flame light of said chemiluminescent radiation disposed between said flame and said light detecting means.

5. A system for detecting compound concentrations in a gas mixture sample which comprises:
   a flame holder;
   a flame chamber within which said flame holder is disposed;
   means for continuously transferring hydrogen to said flame chamber, thus generating a flame and causing chemiluminescent radiation;
   means for detecting light from said chemiluminescent radiation for measuring signals indicative of compound concentrations in the sample; and
   optical shutter means disposed between the flame chamber and said light detecting means for alternately exposing and obscuring the chemiluminescent radiation emitted from said flame chamber while continuously exposing the flame to said light detecting means.

6. The system as set forth in claim 5, which further comprises:
   a stationary chemiluminescent radiation mask member secured to said flame chamber, disposed above and adjacent to said flame as well as between said reaction chamber and said means for detecting light.

7. A system as set forth in claim 5, wherein:
   said optical shutter means comprising a plurality of rotatable shutter blade members, said shutter blade members including arcuate openings for exposing said flame and said chemiluminescent radiation radiation such that the combination of said stationary mask member and said openings obscure said chemiluminescent radiation when said shutter blade members are disposed between said flame chamber and said means for detecting light.

8. A system as set forth in claim 5, which further comprises:
   means for collimating flame light of said chemiluminescent radiation disposed between said flame and said light detecting means.

9. A method for measuring a compound in a gas mixture sample, comprising the steps of:
   continuously introducing the sample into a flame chamber;
   continuously reacting the sample with a preselected reactant for generating a flame and an associated chemiluminescent radiation;
   continuously alternately exposing and obscuring chemiluminescent radiation while continually exposing the flame; and
   continuously measuring light emission resulting from said continuously alternately exposed and obscured chemiluminescent radiation and continually exposed flame.

10. The method as set forth in claim 9, further comprising the step of:
collimating said light emission resulting from said continuously alternately exposed and obscured chemiluminescent radiation and continually exposed flame.

11. A method for measuring sulfur in a gas mixture sample, comprising the steps of:
continuously introducing the sample into a flame chamber;
continuously reacting the sample with a hydrogen reactant for generating a flame so as to cause chemiluminescence of the sulfur and an associated chemiluminescent radiation;
continuously alternately exposing and obscuring the chemiluminescent radiation while continually exposing the flame; and
continuously measuring light emission resulting from said continuously alternately exposed and obscured chemiluminescent radiation and continually exposed flame.

* * * * *